US006932842B1

(12) United States Patent
Litschko et al.

(10) Patent No.: US 6,932,842 B1
(45) Date of Patent: Aug. 23, 2005

(54) METHOD FOR GENERATING PATIENT-SPECIFIC IMPLANTS

(75) Inventors: Peter Litschko, Naumburg (DE); Torsten Henning, Jena (DE); Jörg Beinemann, Weimar (DE); Wolfgang Fried, Jena (DE); Werner Linss, Jena (DE)

(73) Assignee: 3di GmbH, Jena (DE)

( * ) Notice: Subject to any disclaimer, the term of this patent is extended or adjusted under 35 U.S.C. 154(b) by 0 days.

(21) Appl. No.: 10/009,881

(22) PCT Filed: May 10, 2000

(86) PCT No.: PCT/EP00/04166

§ 371 (c)(1),
(2), (4) Date: Jan. 9, 2002

(87) PCT Pub. No.: WO00/68749

PCT Pub. Date: Nov. 16, 2000

(30) Foreign Application Priority Data

May 11, 1999 (DE) ................................ 199 22 279

(51) Int. Cl.[7] ................................................ A61F 2/28
(52) U.S. Cl. ................................... 623/16.11; 623/901
(58) Field of Search ............................ 623/16.11, 901, 623/908; 433/213, 24, 172–176, 201.1; 700/95–98

(56) References Cited

U.S. PATENT DOCUMENTS

| 4,097,935 A | | 7/1978 | Jarcho | |
| 4,436,684 A | * | 3/1984 | White | 264/138 |
| 4,575,805 A | * | 3/1986 | Moermann et al. | 364/474 |
| 4,822,365 A | * | 4/1989 | Walker et al. | 623/20 |
| 4,936,862 A | * | 6/1990 | Walker et al. | 623/23 |
| 4,976,737 A | | 12/1990 | Leake | |
| 5,360,446 A | | 11/1994 | Kennedy | |
| 5,365,996 A | * | 11/1994 | Crook | 164/45 |
| 5,370,692 A | | 12/1994 | Fink et al. | |
| 5,432,703 A | * | 7/1995 | Clynch et al. | 700/163 |

(Continued)

OTHER PUBLICATIONS

Sep. 19, 1997 Die Rekonstruktion kraniofazialer Knochendefekte mit individuellen Titanimplantaten Harald Eufinger et al. Medizin Aktuell 94 A-2407-A2410.

(Continued)

*Primary Examiner*—Kevin Shaver
*Assistant Examiner*—Anu Ramana
(74) *Attorney, Agent, or Firm*—Jordan and Hamburg LLP

(57) ABSTRACT

An implant is generated which is functionally and aesthetically adapted to the patient with a greater degree of precision, irrespective of the size, form and complexity of the defect, whereby the implant can be produced and operatively inserted into the patient over a short time period and in a simple manner. A virtual three-dimensional model of the patient which is formed from existing recorded (two-dimensional) image data of the patient is compared with real medical reference data. The comparison which is, for example, carried out using a data bank with test person data enables a reference model object which is most suited to the patient or closest to the patient model to be selected or formed and a virtual implant model is generated accordingly. Computer numeric control data is directly generated from the implant model which is generated virtually in the computer for program-assisted production of the implant.

10 Claims, 5 Drawing Sheets

U.S. PATENT DOCUMENTS

| | | |
|---|---|---|
| 5,448,489 A | 9/1995 | Reuben |
| 5,452,407 A | 9/1995 | Crook |
| 5,554,190 A | 9/1996 | Draenert |
| 5,687,305 A * | 11/1997 | Graham et al. .............. 345/632 |
| 5,741,215 A | 4/1998 | D'Urso |
| 5,765,561 A * | 6/1998 | Chen et al. ................. 600/407 |
| 5,769,092 A | 6/1998 | Williamson, Jr. |
| 5,798,924 A | 8/1998 | Heuser et al. |
| 5,824,085 A | 10/1998 | Mittelstadt et al. |
| 5,824,111 A * | 10/1998 | Schall et al. .................. 623/33 |
| 6,112,109 A * | 8/2000 | D'Urso ....................... 600/407 |
| 6,254,639 B1 * | 7/2001 | Peckitt .................... 623/11.11 |
| 6,334,853 B1 * | 1/2002 | Kopelman et al. .......... 600/590 |
| 6,463,351 B1 * | 10/2002 | Clynch ....................... 700/163 |

OTHER PUBLICATIONS

Oct. 27, 1999 Stereolithographic biomodelling in cranio-maxillofacial surgery: a prospective trial Paul S. D'Urso, et al. Journal of Cranio-Maxillofacial Surgery 30-37.

Feb. 1999 Schaedelimplantate—computergestuetzte Konstruktion und Fertigung Harald Eufinger, et al. spektrum Der Wiseenschaft 78-81.

* cited by examiner

US 6,932,842 B1

METHOD FOR GENERATING PATIENT-SPECIFIC IMPLANTS

BACKGROUND OF THE INVENTION

The present invention relates to the generation of patient-specific implants based on the examination findings on a patient obtained by imaging methods in medical technology.

It has been possible for long to use, to a limited degree, exogenic material (implants) to close organ defects. The recent state of art is to generate hard-tissue implants specifically adapted to a patient either by obtaining the implants during a surgical operation under use of existing intermediate models or, more recently, under use of CAD/CAM technologies as an aid in computer-aided reconstruction. Imaging methods of the medical technology, such as computer tomography, nuclear magnetic resonance tomography, and sonography increasingly form the basis for generation.

It is common medical practice (refer to, for example, U.S. Pat. No. 4,097,935 and U.S. Pat. No. 4,976,737) to use as implants plastic and workable, respectively, metal webs and metal plates, easily to form materials that have a short curing time (for example, synthetic resin) and endogenic material from the patient by which the defects are closed during the surgical operation, i.e. the implant is obtained during the operation, formed and adapted to the defect. However, metallic implants such as webs and plates etc. can be very disturbing at later diagnosises on the patient and can even render impossible to carry out future special methods of examination, in particular, when larger defect areas are concerned. The progress of operation is usually dependent on the situation of treatment itself, and the experience of the surgeon. In such cases it is scarcely possible to have a specific operation planning for the insertion of the implant in advance. Therefore the operated on patient occasionally has to undergo follow-up treatments that are an additional physical and psychological strain for the patient. Moreover, some materials, such as synthetic materials which are easily to form and/or can be produced at comparatively low expenditures, can only be utilized in a limited degree with respect to their loadability and endurance. Additionally, there is the desire of the patient to get an aesthetic appearance which in many cases is very hard to realize.

Furthermore, "Stereolithographic biomodelling in craniomaxillofacial surgery, a prospective trial", Journal of Cranio-Maxillofacial Surgery, 27, 1999 or U.S. Pat. No. 5,370,692 or U.S. Pat. No. 5,452,407 or U.S. Pat. No. 5,741,215), it is possible to start the design of the implant by generating a physical three-dimensional intermediate model, for example, by stereolithographic methods based on medical imaging methods mentioned at the beginning. Then the implant is manually modeled in the defect site by use of plastic workable materials and only then the implant is finally manufactured from the implant material. Thereby the implant preferably is produced from materials of a higher strength, such as titanium.

Furthermore, there is known ("Schädelimplantate—computergestützte Konstruktion und Fertigung", Spektrum der Wissenschaft, Februar 1999; "Die Rekonstruktion kaniofazialer Knochendefekte mit individuellen Titanimplantaten", Deutsches Ärzteblatt, September 1997), to generate a simple three-dimensional CAD patient model from the data obtained by applying imaging methods on a patient, and to use these data to manually design the implant by computer under use of simple design engineering methods. Subsequently the implant is manufactured for the surgical operation by a computer numeric control (CNC) process.

The methods mentioned hereinbefore, however, have the common disadvantage that the result of the implant-modelling predominantly depends on the experience, the faculty and the "artistic" mastership of the person generating respectively producing said implant. The manufacturing, starting from the data obtained and up to the operationally applicable and mating implant, requires high expenditures of time and cost which are still increased when there is manufactured a so-called intermediate model. The manufacture of an implant during an operation requires correspondingly high expenditures of time and executive routine for the surgical intervention and, thus, means a very high physical and psychological strain, last not least for the patient. Moreover, it is still more difficult to operatively and form-fittingly insert an implant, non-mating to the defect site on the patient, while attending to medical and aesthetic aspects. Also here the special skill and experience of the surgeon very often will be decisive for the outcome of the operation. Practically and in the frame of the clinical routine, the first-mentioned methods can only be used with narrow and/or lowly structurized defects and they will very soon reach their technological limits with complicated defects and implants as concerns shaping and fitting.

The operative expenditure is greatly dependent on the adaptability of the implant to the defect site. But with a manufacture of an implant via intermediate models this precision can be additionally deteriorated due to copying the intermediate model.

In complicated cases the implants have to be manufactured in lengthy and extremely time-consuming processes and, if necessary, via a plurality of intermediate stages. Within this comparatively long period the defect area on the patient can possibly change in the meantime. These changes, in practice, cannot be sufficiently taken into consideration as concerns the adaptability of the implants and additionally increase the operation expenditures.

From the viewpoint of the surgeon as well as of the patient it will be desirable that the implants should be manufactured in the shortest possible time, also with respect to the surgical intervention, and with a high adaptability to the defect site on the patient. Concrete information not only about the defect site on the patient but also to the size and shape of the implant to be inserted should be available to the attending surgeon for planning the operation in advance and before the intervention on the patient.

SUMMARY OF THE INVENTION

It is an object of the present invention to provide an implant generated to be functionally and aesthetically more precisely adaptable to a defect site on a patient, said implant being independent of the size, shape and complexity of said defect site, whereby said implant can be manufactured and inserted into a patient in one operation process in a shorter time and with less expenditures. The method should be applicable with a same accuracy for all shapes, sizes and for all suitable implant materials.

The present invention provides a virtual three-dimensional model of the patient which is compared to actual medical reference data, whereby the model is formed from known (two-dimensional) image data taken at least from its implant area and environment. The model best suited for the patient and a reference model object, respectively, best resembling the model of the patient are selected from this comparison and a virtual implant model is generated according to this model. From the virtual implant model data present in the computer, computer numeric controlled (CNC) data are on-line produced for a program controlled manufacture of the implant. The real-medical reference data can be compared in a database to the medical data taken from a number of probands (third persons) as well as to the data from the patient him/herself, whose body symmetry (in particular mirror-symmetrical body regions, doubly present) is taken into consideration with respect to the selection for and generation of, respectively, a patient reference model. Even data, which do not show this defect or are indicative of changes in the same, can be used for this comparison.

In this way the implant is virtually customized modeled in a very short time under aesthetic and functional aspects and only by computational expenditures (software). Furthermore, the implant is very accurately adapted to the shape of the defect site on the patient as concerns any desired form, size and degree of complexity of the required implant. By means of the virtual implant model, which has been generated and adapted to the defect site and to typical reference data, respectively, by CAD/CAM, the attending surgeon can obtain very concrete data for a physical planning of the operation on the virtual model. He can already simulate the progress of an operation in advance of the intervention so that the proper operation and its progress can be better prepared, carried out and its success evaluated more realistically and, if necessary, to have it discussed with the patient a priori and agreed upon. The implant model is extracted from the virtual reference model of the patient by employing mathematical algorithms. Therefrom the control data for the implant, which has to fill respectively to close the defect site, are on-line deduced.

Thus, the implant can be physically and program-controlled manufactured on-line by exploiting the advantages of CNC which is known per se. Thereby it is not necessary to have any intermediate models or test models (in particular for copying, for tests, for improvements and for corrections as well as for a new manufacture, if necessary). Implants of nearly any desired form and size as well as made of any desired material, including ceramics and titanium, can be manufactured by computer numerical controlled (CNC) production machines into which the data input is computer aided. Thus the implant can be selected for each patient with respect to the required properties (function, strength, absorbability, endurance, aesthetic appearance, biological compatibility etc.). The generation of the implant, which is thus obtained in a very short time and which can be repeated just as quickly under new or changed aspects of the operative intervention, thus reduces the time and routine schedule in the clinical work. Furthermore, the stress for the surgeon and the health risk for the patient are reduced, too. In particular, from the viewpoint of the patient it is a further advantage that a high aesthetic of the implanted defect area is obtained by the accurate adaptation of the implant to be generated to the defective range, and that surgical corrections, refinements as well as other follow-up operations are avoided or at least reduced as to their extent and number.

DETAILED DESCRIPTION OF THE INVENTION

In the following, the invention will be explained in more detail by virtue of the embodiments by reference to the following drawings, in which.

Figure 1:
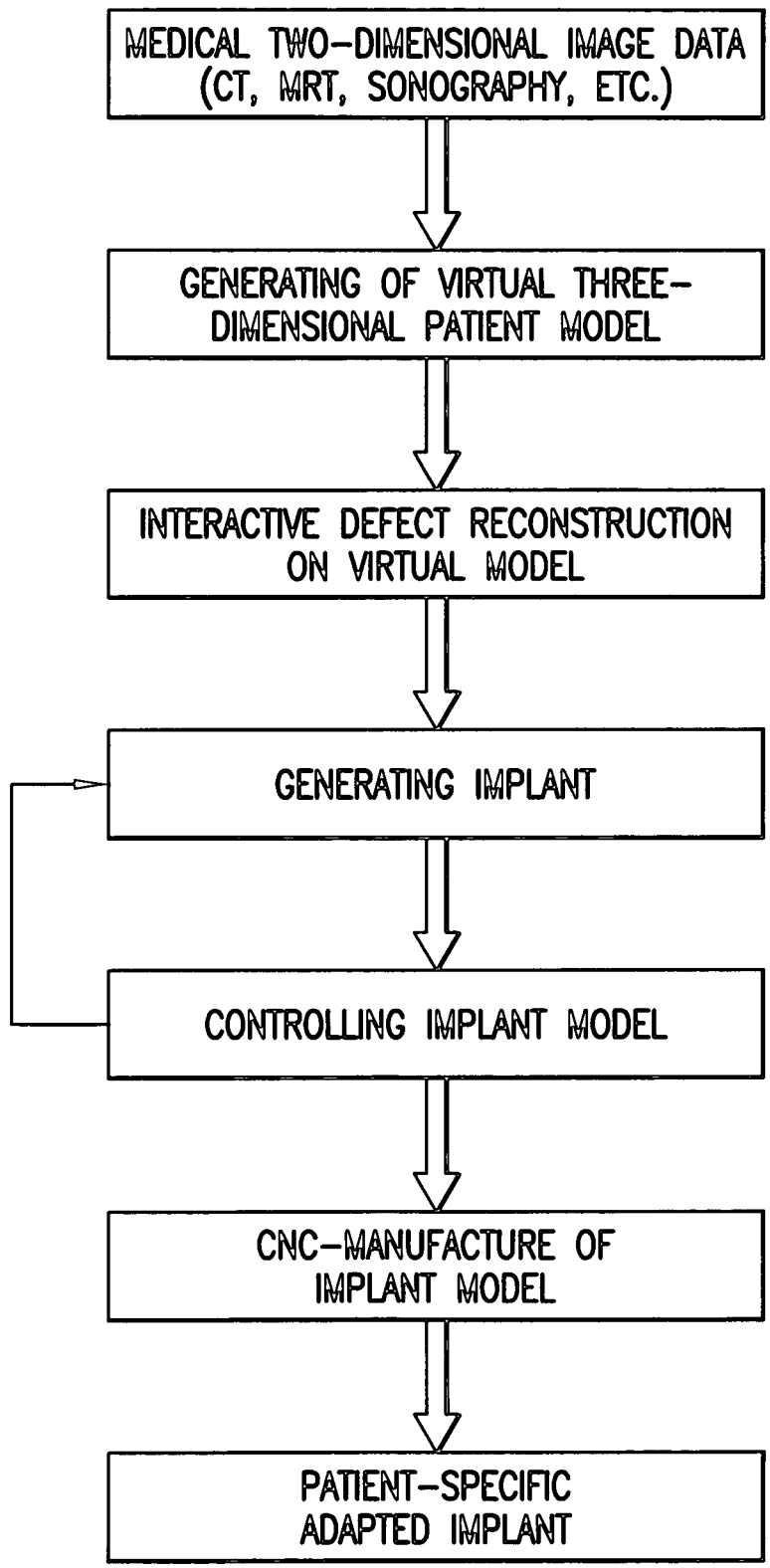
FIG. 1 is a general view of the method according to the present invention.
Figure 2:
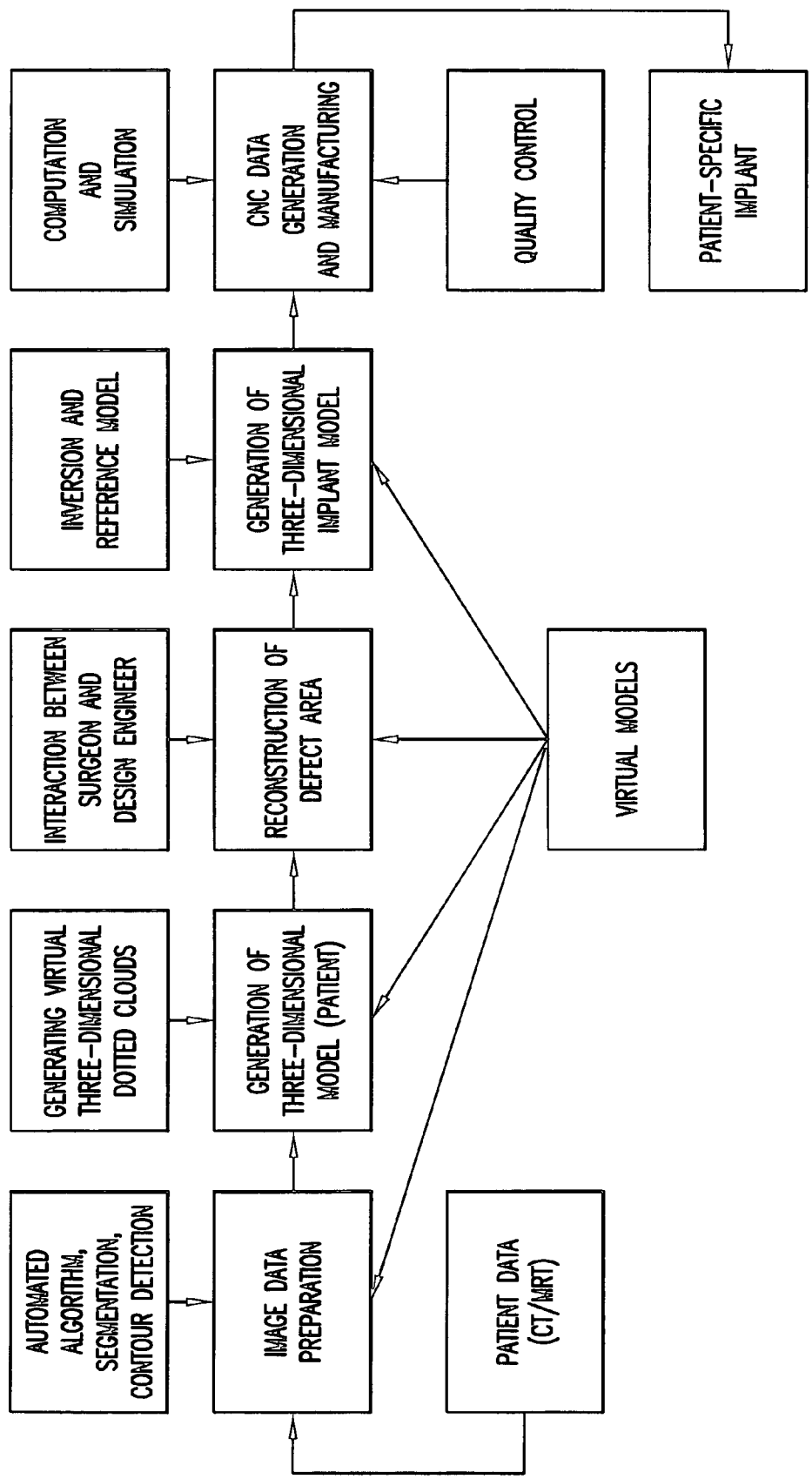
FIG. 2 shows more detail of the general view of the method according to the present invention.

As an example, the case of a patient will be illustrated who has a complicated large area defect (for example, resulting from an accident, a tumor etc.) in the upper half of the cranium. In FIGS. 1 and 2 there are represented both, a general block diagrammatical overview and a detailed block diagrammatical overview to illustrate the method according to the present invention.

Figure 3:
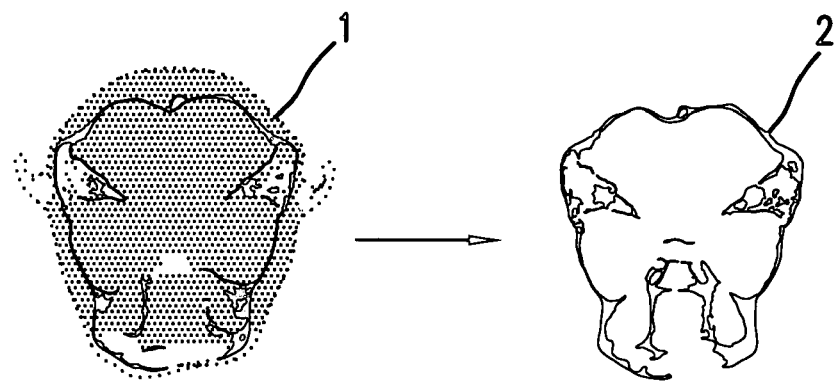
FIG. 3 shows the preparation of medical two-dimensional image data.
Figure 4:
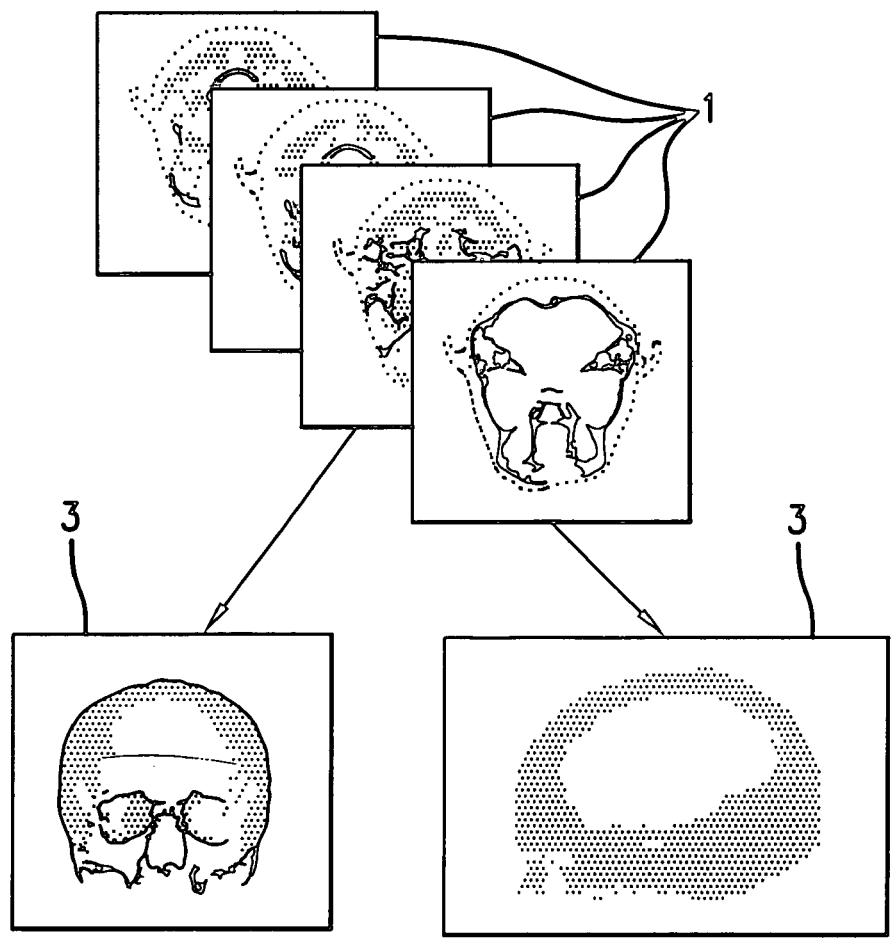
FIG. 4 shows the generation of a three-dimensional patient model.

For a precise diagnosis and for a later implant generation medical two-dimensional image data 1 (two-dimensional tomograms) of a defect area 5 and of the environment of the same (refer to FIG. 3) are taken from a patient in a radiological hospital department (for example by computer tomography or by nuclear magnetic resonance tomography). By use of a mathematical image processing algorithm at first a contour detection is made in the two-dimensional image data 1 and subsequently a segmentation is carried out with the aim to detect the hard tissue ranges (bones). As a result of the contour detection and segmentation two-dimensional image data 2 are obtained via which, by a respective spatial arrangement, a virtual three-dimensional patient model 3 (dotted model) is formed at least of the defect area 5 and environment.

In a cooperation between a physician and a design engineer the defect area is precisely defined and marked in this virtual three-dimensional patient model 3 by utilizing user-specific computer programs especially applicable for this purpose.

Figure 5:
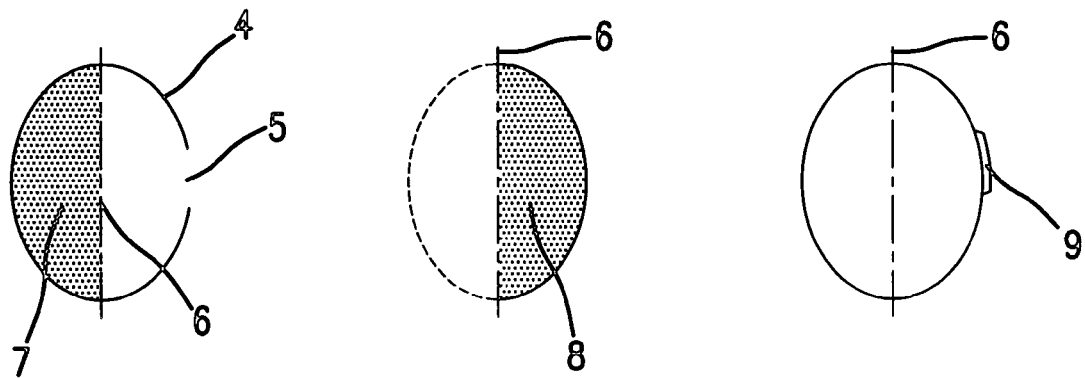
FIG. 5 shows an inversion model.

In the next step, the implant design engineer has several methods at his disposal for generating precisely fitting implants. These methods are:

1. When in a three-dimensional patient model 4 (shown in a cross-sectional view in FIG. 5), the defect area 5 is completely located in one body half, that is, entirely in one head side, then the data of this body side with the defect area 5 can, by inversion, be reconstructed, making use of the bilateral symmetry of the human body, from the data of the undamaged side 7 of the three-dimensional patient model 4 (imaging of the undamaged side 7 at the plane of symmetry 6). After inversion, an extraction of a virtual implant model 9 is carried out by use of mathematical algorithms which will here not be referred to in more detail.

Figure 6:
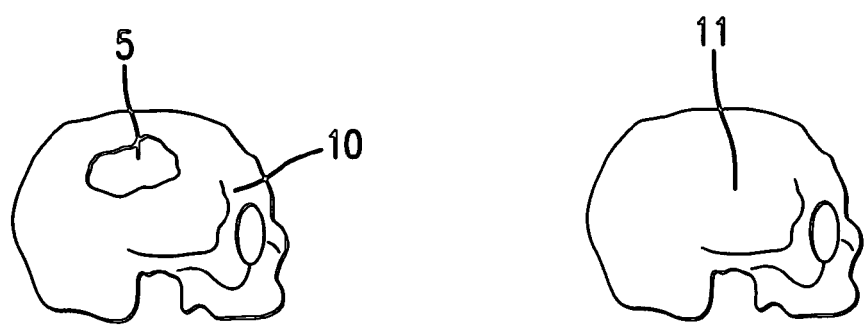
FIG. 6 shows a three-dimensional reference model.
Figure 6:
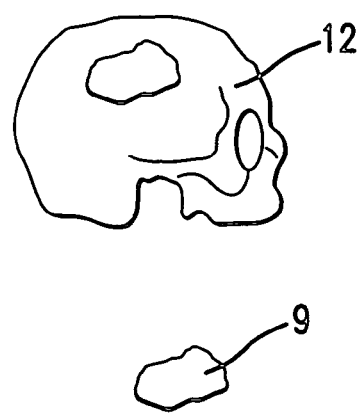

2. When in a three-dimensional patient model 10 (shown in a lateral view in FIG. 6), the defect area 5 is located in the plane of symmetry of the human body or the data of the undamaged side cannot be utilized, somehow or other, then the virtual implant model 9 can be generated via a three-dimensional reference model 11. To this end, specific features of the three-dimensional patient model 10 are compared to a reference database and a selection of similar models is made under consideration of mathematical, functional, medical and aesthetic aspects. To form the similar models, sets of the reference data are selected and corresponding models are formed therefrom most resembling the patient considering the above aspects. Then, the three-dimensional reference model 11 is selected from this range of models, preferably under particular consideration of the medical expert opinion so that the reference model 11 best suited for the patient is selected. By superimposing the three-dimensional reference model 11 and the three-dimensional patient model 10 to one another, a virtual three-dimensional patient model 12 will be obtained, from which, in turn, the virtual implant model 9 will be generated by computer, as described under item 1.

3. In special cases, when for example the defect partially lies in the plane of symmetry, both methods (inversion according to item 1 and database comparison according to item 2) can be used one after the other and the results will be combined to a three-dimensional reference model for the implant modeling.

The selection and/or the shaping of the three-dimensional reference model after at least one of the methods mentioned hereinabove and the generation of the virtual implant model from the three-dimensional reference model are performed merely by computation. By this processing both, a very rapid and a very precisely fitting generation and subsequent manufacture of the implant for the operative insert on the patient is given.

Figure 7:
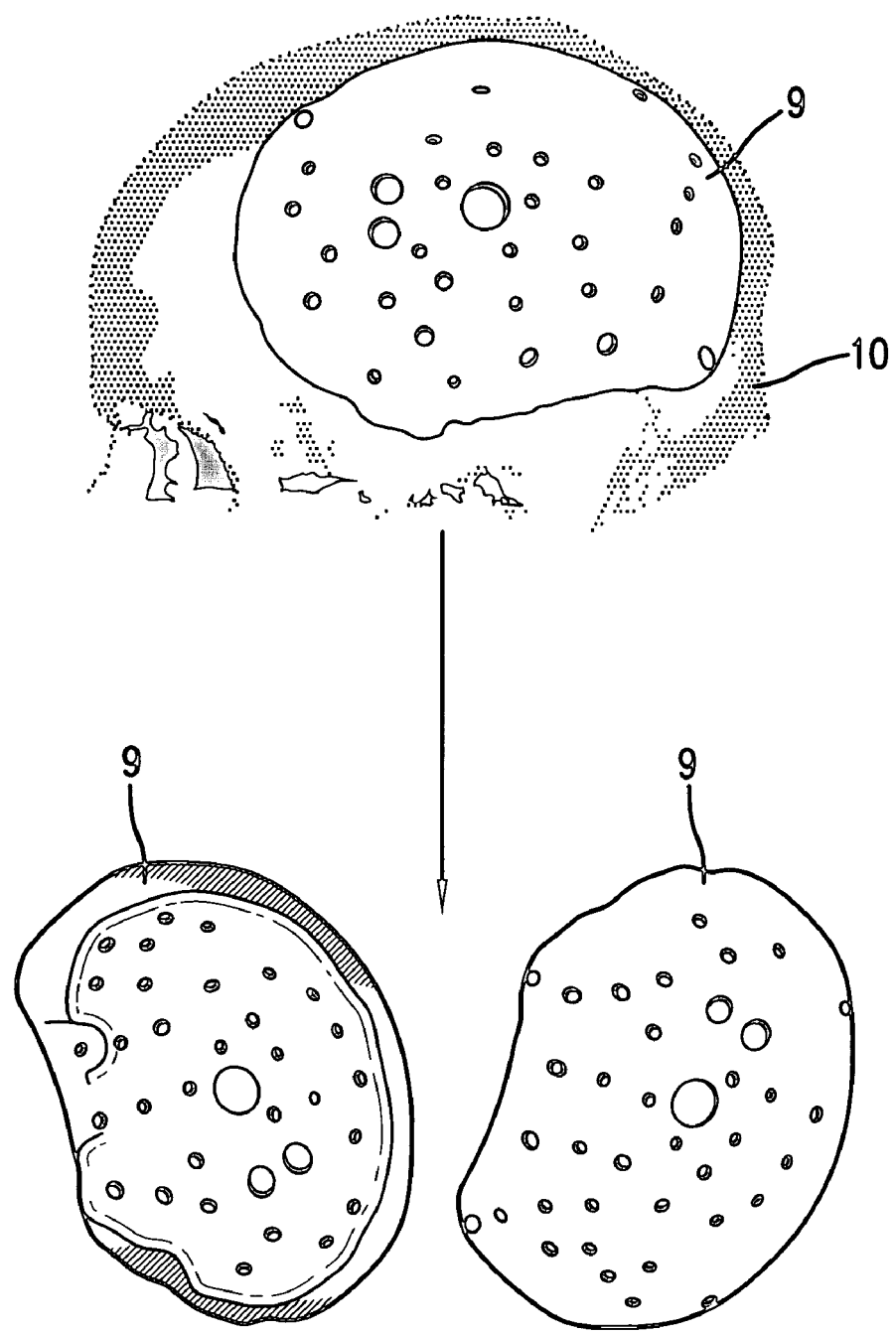
FIG. 7 shows a three-dimensional implant model.

The present virtual implant model 9 (FIG. 7) is subjected to various procedures after its generation. Said procedures may include, for example, strength calculations, simulations for the medical operation planning and the manufacture, as well as providing markings (bore holes, fixings or the like), quality control etc.

After designing the virtual implant model 9, a generation/simulation of the CNC-data for the physical implant manufacture and the transfer of the virtual implant model into a usable implant are carried out.

List of Reference Numerals
1—medical two-dimensional image data
2—contour detection and segmentation two-dimensional image data
3—three-dimensional patient model (dotted model)
4—three-dimensional patient model (cross-section)
5—defect area
6—plane of symmetry of human body
7—undamaged side of the three-dimensional patient model
8—inversion of undamaged side 7
9—(virtual) implant model
10—three-dimensional patient model (lateral view)
11—three-dimensional reference model
12—(virtual) three-dimensional patient model

What is claimed is:

1. Method for manufacturing a patient-specific implant, comprising:
    obtaining medical two-dimensional image data of a defect area in a patient requiring an implant and an environment thereof for a patient by a method selected from the group consisting of computer tomography (CT) and nuclear magnetic resonance (NMR) tomography;
    using a mathematical image processing algorithm to form a surface using the two-dimensional image data;
    performing a segmentation to detect bones and hard tissue ranges;
    generating a virtual three-dimensional model from the image data of at least the defect area in the patient requiring an implant and the environment thereof;
    comparing the virtual three-dimensional model to real medical reference data;
    selecting from the real medical reference data a set of said reference data best suited for the patient and forming a three-dimensional reference model object therefrom, the step of selecting the set of said reference data best suited for the patient and forming a reference model object therefrom comprising:
        first selecting a plurality of sets of the reference data and forming a corresponding plurality of three-dimensional reference model objects therefrom most resembling the patient considering mathematical, functional, medical and aesthetic parameters; and
        then selecting one of said plurality of three-dimensional reference model objects best suited for the patient;
    generating a virtual implant model from said selected one of said plurality of three-dimensional reference model objects by superimposing said selected one of said plurality of three-dimensional reference model objects with the virtual three-dimensional model; and
    manufacturing the implant by computer numeric control based on data from the virtual implant model.

2. Method as claimed in claim 1, wherein the real medical reference data comprise a database.

3. Method as claimed in claim 1 or 2, wherein the real medical reference data comprises data from the patient.

4. Method as claimed in claim 1, wherein the virtual implant model is a three-dimensional virtual implant model.

5. Method as claimed in claim 1, wherein the selection of one of said plurality of three-dimensional reference model objects best suited for the patient is made in consideration of an expert medical opinion.

6. Method for manufacturing a patient-specific implant, comprising:
    obtaining medical two-dimensional image data of a defect area in a patient requiring an implant and an environment thereof for a patient by a method selected from the group consisting of computer tomography (CT) and nuclear magnetic resonance (NMR) tomography;
    using a mathematical image processing algorithm to form a surface using the two-dimensional image data;
    performing a segmentation to detect bones and hard tissue ranges;
    generating a virtual three-dimensional model from the image data of at least the defect area in the patient requiring an implant and the environment thereof;
    comparing the virtual three-dimensional model to real medical reference data;
    selecting from the real medical reference data a set of said reference data best suited for the patient and forming a three-dimensional reference model object therefrom, the step of selecting the set of said reference data best suited for the patient and forming a reference model object therefrom comprising:
        first selecting a plurality of three-dimensional reference model objects similar to the virtual three-dimensional model considering mathematical, functional, medical and aesthetic parameters; and
        then selecting one of said plurality of three-dimensional reference model objects best suited for the patient;
    generating a virtual implant model from said selected one of said plurality of three-dimensional reference model objects by superimposing said selected one of said plurality of three-dimensional reference model objects with the virtual three-dimensional model; and
    manufacturing the implant by computer numeric control based on data from the virtual implant model.

7. Method as claimed in claim 6, wherein the real medical reference data comprise a database.

8. Method as claimed in claim 6, wherein the real medical reference data comprises data from the patient.

9. Method as claimed in claim 6, wherein the virtual implant model is a three-dimensional implant model.

10. Method as claimed in claim 6, wherein the selection of one of said plurality of three-dimensional reference model objects best suited for the patient is made in consideration of an expert medical opinion.

* * * * *